United States Patent [19]
Bhatia et al.

[11] Patent Number: 5,196,551
[45] Date of Patent: * Mar. 23, 1993

[54] CO-VAPORIZATION PROCESS FOR PREPARING LACTIDE

[75] Inventors: Kamlesh K. Bhatia, Newark; James V. Tarbell, Hockessin, both of Del.

[73] Assignee: E. I. du Pont de Nemours and Company, Wilmington, Del.

[*] Notice: The portion of the term of this patent subsequent to Jun. 11, 2008 has been disclaimed.

[21] Appl. No.: 719,952

[22] Filed: Jun. 24, 1991

[51] Int. Cl.$^5$ ............................................ C07D 319/00
[52] U.S. Cl. .................................................... 549/274
[58] Field of Search ......................................... 549/274

[56] References Cited

U.S. PATENT DOCUMENTS

| 1,095,205 | 5/1914 | Gruter et al. | |
| 2,668,163 | 2/1954 | Lowe | 260/78 |
| 4,727,163 | 2/1988 | Bellis | 549/274 |
| 4,835,293 | 5/1989 | Bhatia | 549/274 |
| 5,023,349 | 6/1991 | Bhatia | 549/274 |

FOREIGN PATENT DOCUMENTS 3632103 3/1988 Fed. Rep. of Germany .
3708915 9/1988 Fed. Rep. of Germany .

Primary Examiner—Nicky Chan

[57] ABSTRACT

A distillation process for converting lactic acid oligomer to lactide wherein the oligomer is depolymerized in the presence of a co-vaporizable solvent at a temperature and pressure which forms a vapor fraction comprising water, lactide, lactic acid and solvent, and the vapor fraction is condensed and the lactide is recovered from the condensate.

9 Claims, 1 Drawing Sheet

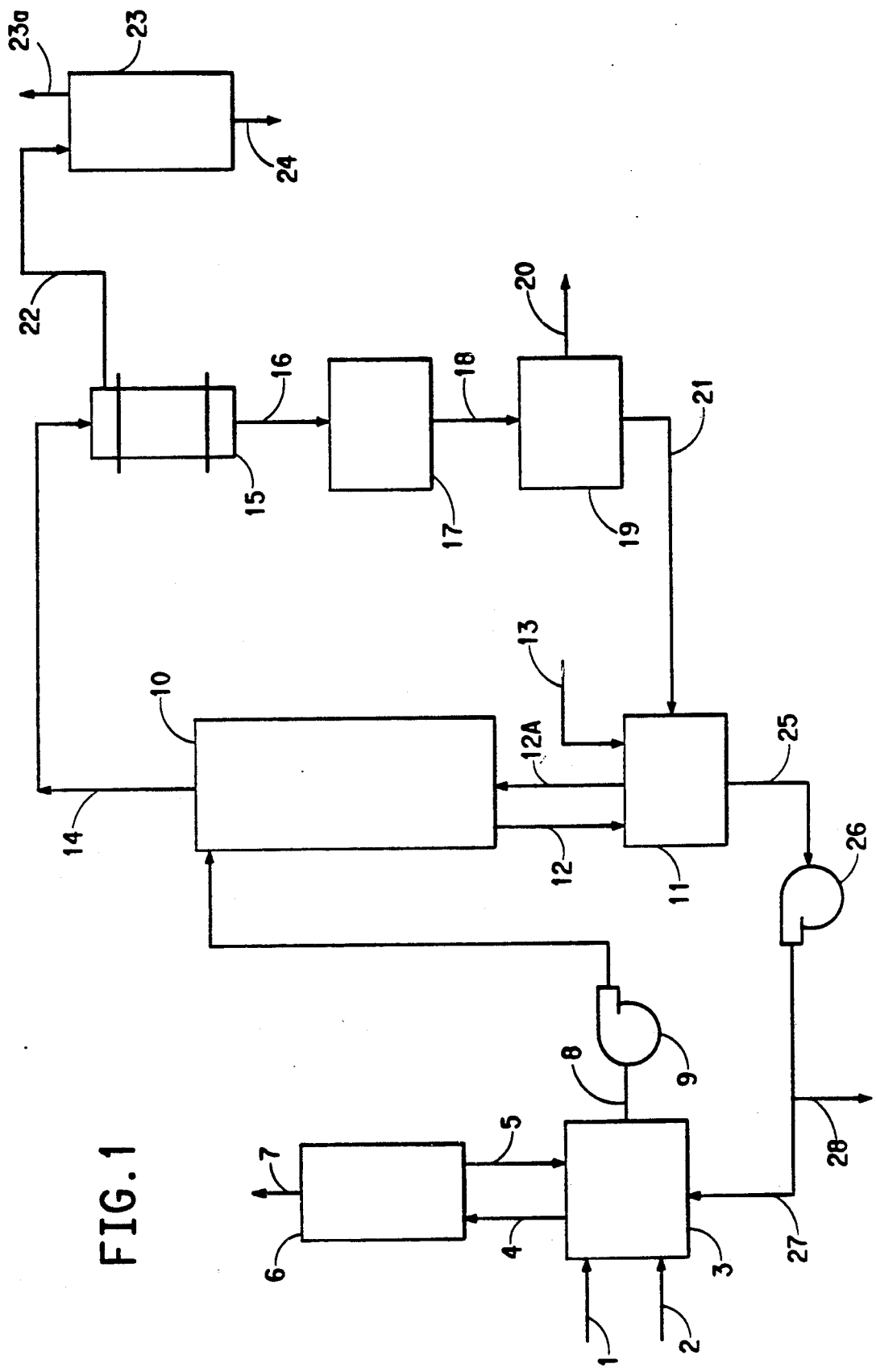

CO-VAPORIZATION PROCESS FOR PREPARING LACTIDE

FIELD OF THE INVENTION

This invention relates to a process for depolymerizing an oligomer of lactic acid to lactide, and, more particularly, it relates to a distillation process wherein depolymerization is conducted in the presence of a "co-vaporizable" solvent at a temperature and pressure at which an overhead vapor fraction is formed which comprises water, lactide, lactic acid and solvent. The overhead vapor fraction is then condensed, and the lactide is recovered from the condensed phase.

BACKGROUND OF THE INVENTION

Lactide is polymerizable to high molecular weight polylactic acids which are of great interest for their hydrolytic and biodegradable properties. Such polylactic acids have long been of interest for biomedical uses as sutures and staples. More recently, they have become of interest for the manufacture of articles for non-biomedical uses in which the article would be hydrolytically degradable in the environment to one or more environmentally acceptable waste materials. For most, if not all such uses, it is preferred that the degradable polymer be made from L-lactide. However, lactide made by existing process technology can be very expensive versus alternative materials for non-medical uses because yields can be low and unwanted by-products tend to form during the reaction.

Lactide is most conveniently prepared by polymerizing lactic acid to a relatively low molecular weight oligomeric polylactic acid, which is then heated, generally in the presence of a catalyst to depolymerize it to lactide, i.e., a cyclic dimer which contains two [OCH(CH$_3$)CO] units, which is then recovered as a component of a vapor product stream. Processing techniques of this type can be seen, for example, in the following references: Gruter et al., U.S. Pat. No. 1,095,205 (1914); Lowe, U.S. Pat. No. 2,668,163 (1954); Bhatia, U.S. Pat. No. 4,835,293 (1989); Bellis, U.S. Pat. No. 4,727,163 (1988); and Muller, Ger. Pat. Applications 3632103 and 3708915 (1988). The prior art processes, however, can entail several drawbacks:

In the depolymerization of a low molecular weight oligomer formed from lactic acid, water and acid impurities can also be formed so that the depolymerization product generally contains these hydroxylic impurities. Impurities of this type can act as chain-stoppers in subsequent polymerization of the lactide to high molecular weight polymers required for biomedical and other uses. Therefore, it is desirable to keep the water and lactic acid contents of the lactide product as low as practicable.

The prior art depolymerization processes can require relatively long reaction times at high temperatures. These conditions can often result in side reactions, leading, for example, to unwanted isomers, including meso lactide, as well as charring of the polymer and consequently difficult-to-handle reactor heels.

SUMMARY OF THE INVENTION

The present invention is a co-vaporization process for converting lactic acid oligomer to lactide, which comprises the steps of:

(i) heating an oligomer of lactic acid in the presence of a depolymerization catalyst and an inert solvent at a temperature and pressure effective to vaporize the solvent and depolymerize the oligomer to lactide while forming an overhead vapor fraction which contains water, lactic acid, lactide and solvent, the solvent being selected such that (a) it is distillable with lactide at the depolymerization temperature, (b) it exerts a vapor pressure such that the sum of the respective solvent and lactide vapor pressures equals or exceeds the operating pressure in the reaction vessel or reaction zone, and (c) is condensable at ambient temperatures;

(ii) condensing the vapor fraction, and (iii) recovering the lactide from the condensate.

The lactide can be recovered from the condensed phase, i.e., the condensate, by any convenient means known to the art. The term "co-vaporization" is used herein to indicate that during operation of the process, lactide and solvent are both present in the vapor fraction, i.e., they are co-vaporized.

According to one aspect of the process, the co-vaporizable solvent functions to facilitate distillative removal of water from the system, and preferably is also a solvent for the oligomer being depolymerized, which generally reduces the viscosity of the depolymerization reaction mass and results in a faster lactide-stripping and production rate.

According to another aspect of the invention, the solvent is water-immiscible, is a solvent for the lactide at a first temperature that is sufficiently low to condense solvent, lactide and water, and is a relatively poor solvent for the lactide at a second temperature that is lower than the first temperature.

The overhead vapor fraction is condensed at said first temperature to form a solvent phase consisting essentially of lactide, solvent and little or no lactic acid and an aqueous phase consisting essentially of water, lactic acid and little or no solvent. The phases are then separated, the solvent phase is cooled to said second temperature to crystallize lactide, and the lactide crystals are separated from the solvent. Alternatively, the solvent phase can be concentrated with vaporization, and cooled if needed, to crystallize the lactide from the solvent.

In another aspect, the solvent is condensible with the lactide and lactic acid values at a temperature sufficiently high to maintain water present in the vapor state. The overhead vapor fraction from the depolymerization step is condensed at such temperature to form a condensed phase containing the solvent, lactide and lactic acid values. If desired, the temperature can be selected such that the water evolved is not condensed and passes overhead as vapor, usually along with some solvent. The condensed phase may be a solution of the lactide and the lactic acid values in the solvent. The lactic acid values may be removed by extraction with water, and the remaining solvent phase can then be cooled to crystallize the lactide or concentrated by evaporation to separate and recover the lactide from the solvent. Where the condensed overhead fraction consists essentially of liquid and solid components, these may be separated and worked up by conventional extraction, crystallization and distillation means known in the art.

The solvent should generally be a relatively poor solvent for the lactide and a good solvent for the lactic acid values and any water present in the overhead. In such a case, the overhead fraction can be condensed and the lactide can be crystallized from the solution, if necessary by concentration, leaving any hydroxylic acid impurities in the solvent.

The process of the invention is also applicable to the recovery of glycolide and other dimeric cyclic esters from the depolymerization mass when the corresponding polyhydroxycarboxylic acids are depolymerized under suitable conditions of temperature and catalysis. Such conditions are described in greater detail in Bhatia, U.S. Pat. No. 4,835,293, the teachings of which are incorporated herein by reference.

The invention is illustrated below with respect to the recovery of lactide from a polylactic acid depolymerization mass. The solvent recovered from any of the lactide recovery steps can be recycled to the depolymerization step along with any lactide dissolved therein. Also, the lactic acid phase from any of the above steps can be concentrated and recycled for the production of oligomer, and the depolymerization and co-vaporization step can be conducted in a continuous manner.

Preferably, the oligomer is an oligomer of L-lactic acid and the product is L-lactide.

The co-vaporization process of the invention does not require very low reduced pressure operation, e.g., below 200 mm of Hg, which can increase substantially the cost of operation, and it enables the lactide depolymerization product to be stripped quickly from the oligomeric mass at a rate substantially as fast as it is formed, i.e., conversion rate is very high. Decomposition, racemization and charring of the oligomeric mass are minimized, and water and lactic acid, when present, can be smoothly and substantially completely eliminated from the product stream.

BRIEF DESCRIPTION OF THE DRAWING

FIG. 1 is a schematic flow diagram of the process of the invention according to one embodiment in which a depolymerizer 10 is employed in conjunction with a reboiler 11.

DETAILED DESCRIPTION OF THE INVENTION

The process of the invention is carried out by introducing a lactic acid oligomer into a reaction zone, preferably preheated to a temperature high enough to effectively depolymerize the oligomer to lactide, i.e., to a cyclic dimer which contains 2 preferably [OC(CH$_3$)CO] units. Substantially simultaneously, a vapor stream of a solvent as defined, which may come from a reboiler, is contacted with the liquid mass at the depolymerization temperature. A large interfacial area is formed between the solvent vapors and the depolymerizing oligomer such that the lactide that forms is stripped rapidly from the oligomer. Thus, there is produced a vapor fraction which is a stream comprising solvent, lactide and other volatiles, such as water, lactic acid and vaporizable oligomers thereof, normally also present and a liquid phase, or liquid fraction, which consists of unvaporized oligomer, lactide and condensed solvent. The vapor fraction is removed from the reaction zone and is condensed.

When the solvent employed is a water-immiscible solvent and the quantities of water and acid impurities are sufficiently large so as to form a separate phase when condensed, the impurities can be removed in the separate aqueous phase. Otherwise, the impurities are extracted with water and the lactide is recovered from the solvent phase.

When the solvent employed is one in which the impurities are more soluble therein than the lactide, the lactide can be conveniently recovered by crystallization, leaving the impurities dissolved in the solvent which remains. Lactic acid and its water-soluble dimer, if present, can also be recovered from the aqueous phase by any means known in the art, such as evaporation of the water, and then recycled for use in the process.

The process is applicable to continuous as well as batch operation. The oligomeric material will normally contain from about 2 up to about 15 polymerized lactic acid units, viz.

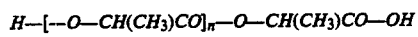

$$H-[-O-CH(CH_3)CO]_n-O-CH(CH_3)CO-OH$$

where n=1 to 14, but ordinarily 5 to 11, and may be prepared by any method known to the art.

The solvent may be any inert liquid which can be condensed, preferably with cooling tower water or air as the coolant, at the operating pressure of the reactor and which allows an operating pressure which is higher than the vapor pressure of lactide over its oligomeric precursor.

For best results, the solvent vapor pressure will be at least that of the lactide, and the normal boiling point of the solvent be below the boiling point of the lactide, i.e. below about 260° C. It is desirable that the temperature of the solvent vapors be maintained at a value which is no higher than 5°–10° C. of the temperature at which the oligomer is being depolymerized to avoid subjecting the depolymerization mass and the lactide product being formed to unnecessary thermal stress.

The solvent should have a relatively high solvency for lactide at the first temperature and a relatively low solvency for it at the second (lower) temperature, and should be stable and inert to all components of the reaction system under process conditions. Typical and representative of solvents which can be used in the process of the invention water-immiscible non-polar solvents having a boiling point which is higher than water, e.g., in the range of from about 170° to 220° C., and preferably at least about 180° C. Included are aromatic hydrocarbons and inert non-reactive derivatives, such as, for example, aromatic hydrocarbons and halohydrocarbons selected from the group consisting of by o-, m- and p-diethylbenzene, m- and p-propyltoluene, 1,2,3-, 1,2,4- and 1,3,5- trimethylbenzene, o- and m-dichlorobenzene, 1,2,4-trichlorobenzene and mixtures of any two or more thereof. The preferred solvent is o-dichlorobenzene (ODCB). Also included are such solvents as nitrobenzene and ketones, esters, ethers and higher alcohols, exemplified by methyl isobutyl ketone, diisobutyl ketone, cyclohexanone, n-amyl acetate, ethyl valerate and ethylene glycol dimethyl ether.

The depolymerization temperature can range from about 170° to about 230° C., but best results have been observed when the depolymerization temperature is at least about 200° C. Temperatures higher than about 230° C. tend to racemize the product when optically active (L- or D-) lactide is desired.

In the preferred lactide recovery procedure, the first temperature (i.e. the temperature at which the overhead stream of water, lactic acid, lactic acid dimer, if any, lactide and solvent is condensed to form two phases as described above) will be lower than the depolymerization and overhead vapor fraction temperature but sufficiently high that the lactide is substantially completely dissolved in the solvent.

This first temperature depends upon the solvent being used, how its solvency for lactide varies with temperature, and the relative proportion of lactide being condensed. The optimum temperature for a given solvent and a given proportion of lactide is readily determined by trial. With ODCB, b.p. 180° C., as the solvent, for example, the condensation temperature may vary widely from a low of about 20° up to 70° C., but ordinarily it will be in the range of from about 40° to 60° C.

The maximum proportion of lactide relative to that of the solvent in the vapor from the reactor can be estimated from the vapor pressure of lactide at the boiling point of the solvent. At 180° C., for example, the normal boiling point of ODCB, the vapor pressure of lactide is 47 mm of Hg. Its maximum proportion in the vapor fraction relative to that of ODCB at atmospheric pressure is estimated to be 47/760 or about 6% so that the condensed organic phase is expected to consist of about 6% lactide and 94% ODCB. In general, the greater the proportion of lactide in the condensed phase the higher should be the condensation temperature to ensure that the lactide will be substantially completely solubilized by the solvent.

If necessary to ensure complete solubility of the lactide in the lactide-ODCB condensate, the vapor fraction can be condensed in an additional quantity of ODCB sufficient for this purpose. Alternatively, ODCB can be added as needed to a two-phase condensate when formed to achieve a homogeneous lactide-ODCB solution.

The pressure throughout the reaction zone may vary from sub-atmospheric, e.g., 200 mm, to atmospheric and super-atmospheric up to a maximum of 2 atmospheres, depending on the boiling point on the particular solvent employed. Carrying out the reaction at a slight super-atmospheric pressure is generally preferred for reasons of economy. A sub-atmospheric pressure of at least 100 mm, or as low as 200 mm of Hg, can be employed depending upon the boiling characteristics of the solvent.

The invention may be better understood with reference to FIG. 1, which schematically depicts the process of the invention comprising a lactic acid-to-oligomer converter in combination with a depolymerizer, means for passing a stream of vaporized solvent as defined through the depolymerizer, exit means through which passes the overhead vapor fraction of water, lactic acid, lactide and solvent, and means for processing the overhead into its respective components.

In a typical operation, concentrated aqueous L-lactic acid, e.g. 88% L-lactic acid as is commercially available, containing 0.45 percent by weight of stannous octoate, is fed through line 1 to dehydrator 3 and o-dichlorobenzene (ODCB), in this exemplification of the invention, is fed to the dehydrator through line 2. The aqueous lactic acid is concentrated by distillation, and then it is oligomerized by gradually heating the reaction mass to about 170° C. Water vapor exits the dehydrator 3 through line 4 to dephlegmator 6, which allows water to pass but condenses lactic acid and ODCB vapors which return as the condensate to the dehydrator 3 via line 5.

The solvent facilitates the oligomerization step and helps provide a fluid oligomeric mass which is pumped through line 8 by pump 9 to the top of depolymerizer 10. The depolymerizer is a columnar sieve plate reactor which is heated to a temperature in the range of about 180° to 220° C. by heating means not shown. The oligomeric mass flows down column 10, and is counter-currently contacted by hot vapors, i.e , 180°-220° C., of ODCB exiting reboiler 11. This produces the vapor fraction comprising ODCB, lactide and minor amounts of lactic acid and water which exits the column overhead through line 14. Oligomer that has not depolymerized, passes to reboiler 11 via line 12 where it can continue to undergo depolymerization to lactide. Lactide produced in reboiler 11 likewise passes via line 12A upwardly into the column along with vaporized ODCB, lactic acid and water also present as part of the overhead vapor fraction exiting via line 14. Fresh ODCB, as needed to maintain a liquid bottoms in the seive plate reactor, is added to the reboiler 11 through line 13. It is desirable that a portion of the solvent vapor condenses in the column which provides some or all the heat needed to vaporize the lactide.

The overhead vapor fraction passes from the seive plate reactor through line 14 to condenser 15 which is maintained at a temperature in the range of from about 40° to about 60° C. where the vapor fraction is condensed, and the condensate comprises a solvent layer consisting essentially of a solution of L-lactide in ODCB and an aqueous layer consisting essentially of water and lactic acid. The lactide/solvent solution passes via line 16 to crystallizer 17 where it is cooled to 40° C. or below to crystallize L-lactide. The L-lactide/ODCB slurry which results is filtered in a filter 19, in which the crystals are washed with ODCB. The lactide crystals are then removed through line 20, and the mother liquor, i.e., filter wash liquor, is returned to the reboiler through line 21. The lactide product, which is substantially L-lactide, can be further purified, if desired and depending on its intended use, by recrystallization from a suitable solvent or by other means known in the art.

The aqueous layer leaving condenser 15 through line 22 enters a concentrator 23 where it is concentrated to 80-90% aqueous L-lactic acid and removed through line 24. Although not shown in the schematic diagram, the lactic acid can be recycled to dehydrator 3 for conversion to oligomer as described above. The condenser gas vent is line 23a. Although not shown in the schematic diagram, this gas would be treated before being vented to the atmosphere.

Similarly, the residue from depolymerizer 10 comprising unconverted oligomer, catalyst, tars and ODCB can be recycled to depolymerizer 10 via dehydrator 3, by means of line 25, pump 26 and line 27. If necessary, to minimize undue build-up of material in reboiler 11 and dehydrator 3, excess tars can be purged periodically through line 28.

In an alternative embodiment the process of the invention can be carried out with satisfactory results when depolymerizer 10 is a packed column or any other reactor design having a reaction zone which promotes intimate vapor-liquid contact. A contemplated equivalent of the process of the invention is an arrangement in which the reboiler is also employed as a depolymerizer, and a separate depolymerizer is then not needed, i.e., the vapor fraction which issues from the reboiler is passed directly to a condenser.

The steps of polymerizing lactic acid to polylactic acid and of depolymerizing polylactic acid to lactide are ordinarily and preferably conducted in the presence of a catalyst. The catalyst can be carried in the lactic acid feed stream or incorporated into the oligomeric mass, and it can be any of those known in the art for promoting condensation of the alpha-hydroxycarboxylic component to oligomers and promoting cyclic ester formation. The catalysts are generally metals or compounds of metals of groups IV, V and VIII of the Periodic Table. Preferred are metals of group IV, notably Sn as the metal (powdered), oxide, halogenide or carboxylate, or group V, notably Sb, usually as the oxide $Sb_2O_3$. Preferred herein are Sn(II) carboxylates, especially those that are soluble in the feed stream and the resulting reaction mixture, exemplified by Sn bis (2-ethylhexanoate), commonly referred to as stannous octoate.

The catalyst is employed in catalytically effective amounts which can vary widely depending upon reaction conditions. The optimum catalytically effective amount for any particular system can readily be determined through trial runs. For example, with Sn (II) octoate as the catalyst, the amount needed is an amount such that the oligomeric mass contains from about 0.1 to 1.5% by weight of the catalyst, but best results are ordinarily achieved when the catalyst is present in the oligomeric mass in an amount of from 0.3 to 0.7% by weight.

We claim:

1. A co-vaporization process for converting lactic acid oligomer to lactide, which comprises:
   (i) heating an oligomer of lactic acid in the presence of a depolymerization catalyst and an water-immiscible high-boiling inert solvent in a reaction zone to a temperature and at a pressure which will vaporize the solvent and depolymerize the oligomer to lactide while forming a vapor fraction comprising water, lactic acid, lactide and solvent, the solvent being selected such that (a) it is distillable with lactide at the temperature at which depolymerization is occurring, and (b) it exerts a vapor pressure such that the sum of the respective solvent and lactide vapor pressures equals or exceeds the operating pressure of the process, and (c) is condensable without using refrigeration;
   (ii) condensing the vapor fraction, and
   (iii) recovering the lactide from the condensate.

2. The process of claim 1 wherein the process includes the additional steps of: (i) condensing the vapor fraction at a first temperature to form a solvent phase consisting essentially of lactide, solvent and little or no lactic acid and an aqueous phase consisting essentially of water, lactic acid and little or no solvent; (ii) separating the solvent phase and crystallizing the lactide by cooling the solvent phase to a second temperature which is lower than the first temperature; and separating the lactide from the solvent.

3. The process of claim 2 which includes the additional step of recycling the solvent to the reaction zone.

4. The process of claim 3 wherein the solvent is an aromatic hydrocarbon or a haloaromatic hydrocarbon having a boiling point in the range of from about 170° C. to about 220° C., and the reaction zone is maintained at a temperature in the range of from about 170° C. to about 230° C.

5. The process of claim 4 wherein the solvent is ortho-dichlorobenzene.

6. The process of claim 1 where the oligomer is an oligomer of L-lactic acid.

7. A vaporization process for depolymerizing a lactic acid oligomer to lactide, which process comprises:
   (i) forming a composition comprising an oligomer of lactic acid, a depolymerization catalyst and an inert high boiling water-immiscible solvent that is co-distillable with lactide at a temperature at which the oligomer depolymerizes, is condensable and is a solvent for lactide at a first temperature and is a non-solvent for lactide at a second, lower temperature;
   (ii) heating the composition of (i) to boiling in a depolymerization zone at a temperature and pressure effective to depolymerize the oligomer and form a vapor fraction comprising water, lactide, solvent and any lactic acid also present in the oligomeric composition; and
       (b) a liquid bottoms phase containing solvent, unconverted oligomer and depolymerization catalyst;
   (iii) condensing the vapor fraction at said first temperature to form a solvent phase consisting essentially of lactide, solvent and little or no lactic acid and an aqueous phase consisting essentially of water, lactic acid and little or no solvent;
   (iv) separating the phases and crystallizing the lactide in the solvent phase; and
   (v) separating the lactide crystals from the solvent.

8. A co-vaporization process for converting lactic acid oligomer to lactide, which process comprises:
   (i) heating an oligomer of lactic acid in the presence of a depolymerization catalyst and vapors of a high-boiling, water-immiscible inert solvent at a temperature and pressure effective to vaporize the solvent and depolymerize the oligomer to lactide and form a vapor fraction containing water, lactic acid, lactide and solvent, the solvent being selected such that
       (a) it is distillable with lactide at the depolymerization temperature,
       (b) is condensible and is a solvent for lactide at a first temperature which is below the temperature at which depolymerization occurs but sufficiently high to maintain water in the vapor state, and
       (c) is a relatively poor solvent for lactide at a second temperature that is lower than the first temperature;
   (ii) partially condensing the vapor fraction at said first temperature to form a liquid phase consisting essentially of lactide, solvent and lactic acid and a vapor phase consisting essentially of water and little or no solvent or lactic acid;
   (iii) cooling the liquid phase to said second temperature to crystallize the lactide; and
   (iv) separating the lactide crystals from the solvent.

9. A co-vaporization process for converting lactic acid oligomer to lactide which comprises:
   (i) introducing a lactic acid oligomer, which has been preheated to a temperature high enough to effectively depolymerize it to lactide, into a reaction zone maintained at the depolymerization temperature;
   (ii) substantially simultaneously contacting the preheated oligomer in the reaction zone with a vapor stream comprising a water-immiscible high-boiling inert solvent in a manner whereby a large interfacial area is formed between the solvent vapors and the depolymerizing oligomer to rapidly strip the lactide from the oligomer and thereby produce a vapor fraction comprising solvent, lactide, water and lactic acid and a liquid fraction comprising unvaporized oligomer, lactide and condensed solvent;
   (iii) removing the vapor fraction from the reaction zone;
   (iv) condensing the vapor fraction; and
   (v) recovering the lactide from the condensate.

* * * * *